(12) United States Patent
Lalonde

(10) Patent No.: US 9,011,420 B2
(45) Date of Patent: Apr. 21, 2015

(54) COMPATIBLE CRYOGENIC COOLING SYSTEM

(75) Inventor: Jean-Pierre Lalonde, Candiac (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1168 days.

(21) Appl. No.: 12/913,281

(22) Filed: Oct. 27, 2010

(65) Prior Publication Data

US 2012/0109119 A1 May 3, 2012

(51) Int. Cl.
*A61B 18/02* (2006.01)
*A61B 18/00* (2006.01)

(52) U.S. Cl.
CPC ....... *A61B 18/02* (2013.01); *A61B 2018/00214* (2013.01); *A61B 2018/0212* (2013.01); *A61B 2018/0262* (2013.01)

(58) Field of Classification Search
CPC ........... A61B 2018/00005; A61B 2018/00011; A61B 2018/00023; A61B 1028/0262; A61B 2018/0212; A61B 18/02; A61F 7/12
USPC .......................... 606/20, 22, 25; 607/104, 105
See application file for complete search history.

(56) References Cited

U.S. PATENT DOCUMENTS

| | | | | |
|---|---|---|---|---|
| 4,296,610 A * | 10/1981 | Davis | ............................... | 62/50.1 |
| 4,376,376 A * | 3/1983 | Gregory | .......................... | 62/48.1 |
| 4,640,323 A | 2/1987 | Norcia et al. | | |
| 5,452,582 A * | 9/1995 | Longsworth | .................... | 62/51.2 |
| 5,603,221 A * | 2/1997 | Maytal | ............................. | 62/51.2 |
| 6,266,995 B1 * | 7/2001 | Scott | .............................. | 73/23.2 |
| 6,387,161 B1 | 5/2002 | Zhou et al. | | |
| 6,471,694 B1 * | 10/2002 | Kudaravalli et al. | ............ | 606/21 |
| 6,585,729 B1 * | 7/2003 | Eum | ............................... | 606/22 |
| 6,635,053 B1 * | 10/2003 | Lalonde et al. | ................. | 606/22 |
| 7,004,936 B2 * | 2/2006 | Ryba et al. | ....................... | 606/20 |
| RE40,868 E * | 8/2009 | Ryba et al. | ....................... | 606/20 |
| 2008/0119834 A1 * | 5/2008 | Vancelette et al. | .............. | 606/20 |
| 2009/0171333 A1 | 7/2009 | Hon | | |
| 2009/0194103 A1 * | 8/2009 | Thom et al. | ............. | 128/203.12 |
| 2013/0245359 A1 * | 9/2013 | Brault | ............................. | 600/13 |

FOREIGN PATENT DOCUMENTS

| | | |
|---|---|---|
| CN | 101194854 A | 6/2008 |
| CN | 101652107 B | 8/2011 |
| EP | 0038673 A2 | 10/1981 |
| GB | 1244276 | 8/1971 |
| WO | 0213710 A1 | 2/2002 |

OTHER PUBLICATIONS

Maquet, Central Gas Supply Systems Medap-Med Gas, Brochure.
Supplementary European Search Report dated Mar. 12, 2014 for Application No. EP 11 83 5372, consisting of 2 pages.
Notice on the First Office Action, Application/Patent No: 201180051198.0, Applicant/Patenee: Medtronic Cryocath LP, Title: Compatible Cryogenic Cooling System, Nov. 4, 2014, 8 pages.

* cited by examiner

*Primary Examiner* — Joseph Stoklosa
*Assistant Examiner* — Jocelyn D Ram
(74) *Attorney, Agent, or Firm* — Christopher & Weisberg, P.A.

(57) ABSTRACT

A method of operating a medical system, including coupling a medical system to an outlet of a fluid distribution network having a plurality of fluid outlets in a patient treatment center; delivering fluid from the outlet to the medical system; compressing the delivered fluid with the medical system; decreasing the moisture content of the delivered fluid with the medical system; cooling the fluid with the medical system; delivering the fluid from the medical system to a medical device; and removing the fluid from medical device with the medical system.

12 Claims, 3 Drawing Sheets

COMPATIBLE CRYOGENIC COOLING SYSTEM

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a medical coolant system and methods of use thereof, and more particularly, towards a cryogenic coolant system for use with medical devices to treat or ablate tissue.

BACKGROUND OF THE INVENTION

A number of cooled catheter systems have been developed for treating patients. Such systems may provide a variety of cryogenic and/or cooling treatment or diagnostic procedures, including cooling a desired tissue region, such as a portion of the heart, to stun it and allow cold mapping of the heart and/or confirmation of a catheter position with respect to localized tissue lesions, or to apply a more severe level of cold to ablate tissue at the site of the catheter ending.

In general, when used for endovascular access to treat the cardiac wall, catheters of this type, in common with the corresponding earlier-developed radio frequency or electrothermal ablation catheter, must meet fairly demanding limitations regarding their size, flexibility, and the factors of strength, electrical conductivity and the like which affect their safety and may give rise to failure modes in use. These constraints generally require that the catheter be no larger than several millimeters in diameter so as to pass through the vascular system of the patient to the heart. Thus, any electrodes (in the case of mapping or RF/electrothermal ablation catheters), and any coolant passages (in the case of cryocatheters) must fit within a catheter body of small size.

A number of different fluids have been used for the coolant component of prior art cryotreatment catheters, such as a concentrated saline solution or other liquid of suitably low freezing point and viscosity, and of suitably high thermal conductivity and heat capacity, or a liquified gas such as liquid nitrogen. In all such constructions, the coolant must circulate through the catheter, thus necessitating multiple passages leading to the cooling area of the tip from the catheter handle.

Furthermore, conditions of patient safety must be considered, raising numerous problems or design constraints for each particular system. Thus for example, a high pressure may be required to circulate sufficient coolant through the catheter body to its tip and back, and the overall design of a catheter must be such that fracture of the catheter wall or leakage of the coolant either does not occur, or if it occurs, is harmless. Further, for an endovascular catheter construction, the presence of the coolant and circulation system should not substantially impair the flexibility or maneuverability of the catheter tip and body.

To some extent these considerations have been addressed by using a phase change material as the cryogenic fluid, and arranging the catheter such that the phase change, e.g., from a liquid to a gas, occurs in the treatment portion of the catheter tip. Another possible approach is to employ a pressurized gas, and configure the catheter for cooling by expansion of the gas in the tip structure. However, owing to the small size that such a catheter is required to assume for vascular insertion, or the awkwardness of handling a cryogenic treatment probe generally, the design of a safe and effective coolant circulation system which nonetheless dependably provides sufficient cooling capacity at a remote tip remains a difficult goal.

Moreover, when specialized fluids or coolants are selected for use, they are often available only in large, industrial-size containers that can take up a significant amount of space in an operating room or electrophysiology lab. In addition, if the coolant or tank provides for a limited number of procedures before needing to be re-filled or replaced, a hospital or treatment center may need to store numerous containers of the selected fluid or coolant to treat a steady stream of patients. Such storage and/or frequent replacement of one coolant tank with another can greatly increase the cost and reduce the efficiency of maintaining and operating a particular medical cooling system and associated devices.

Accordingly, it would be desirable to provide a coolant system that can be effectively and efficiently integrated into or otherwise used with existing fluid source systems within a hospital or treatment center to avoid the undesired costs and efforts associated with the frequent re-filling or replacing of coolant sources in medical cooling systems.

SUMMARY OF THE INVENTION

The present invention advantageously provides a medical cooling system for use in association with a fluid distribution network having a plurality of fluid outlets in communication with a central supply, the medical cooling system including a fluid delivery conduit defining an inlet engageable with one of the fluid outlets and an outlet engageable with a medical device; a compressor in fluid communication with the fluid delivery conduit; an adsorbent element disposed in the fluid delivery conduit; and a subcooler in thermal communication with the fluid delivery conduit. The system may include a medical device coupled to the outlet of the fluid delivery conduit, where the medical device is a cryogenic treatment device. The compressor may operate to compress a fluid, such as nitrous oxide, received from the fluid outlet to a pressure between approximately 500 psig to 1,000 psig, and the adsorbent element may reduce a humidity level of a fluid received from the fluid outlet to approximately 60 ppm or less. The system may include a reservoir downstream of the compressor and in fluid communication with the fluid delivery conduit; a fluid return conduit engageable with the medical device; a vacuum pump coupled to the fluid return conduit; and/or a flow meter coupled to the fluid delivery conduit.

A method of operating a medical cooling system is provided, including coupling a medical cooling system to an outlet of a fluid distribution network having a plurality of fluid outlets in communication with a central supply; delivering fluid from the outlet to the medical cooling system; compressing the delivered fluid with the medical cooling system; and decreasing the moisture content of the delivered fluid with the medical cooling system. The method may include liquefying the fluid with the medical cooling system; storing the fluid in the medical cooling system for use in a medical procedure; delivering the fluid from the medical cooling system to a medical device; and/or removing the fluid from medical device with the medical cooling system.

A method of operating a medical system is provided, including coupling a medical system to an outlet of a fluid distribution network having a plurality of fluid outlets in a patient treatment center; delivering fluid from the outlet to the medical system; compressing the delivered fluid with the medical system; decreasing the moisture content of the delivered fluid with the medical system; cooling the fluid with the medical system; delivering the fluid from the medical system to a medical device; and removing the fluid from medical device with the medical system.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
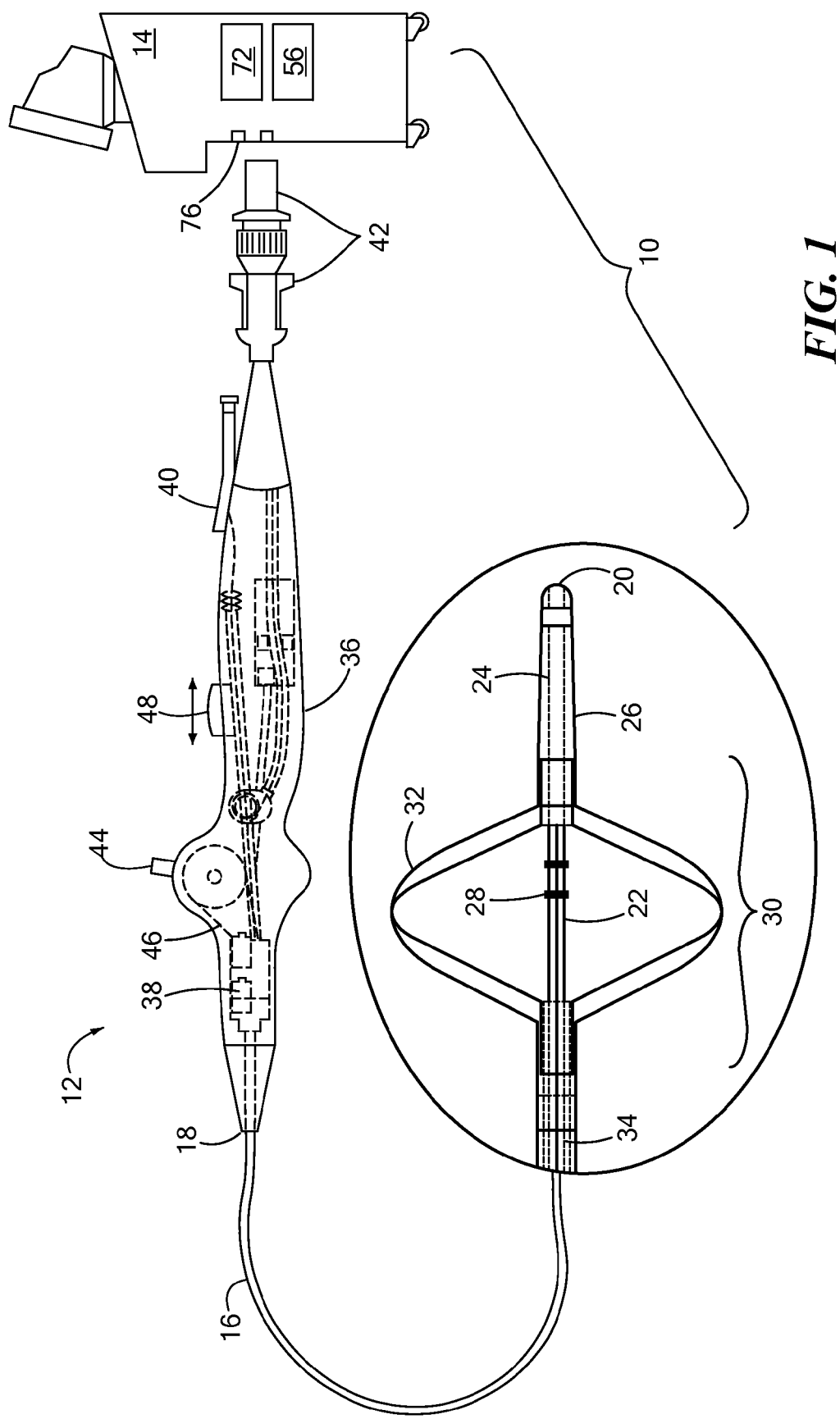
FIG. 1 is an illustration of an embodiment of a medical system constructed in accordance with the principles of the present invention.

The present invention provides a medical cooling system that can be effectively and efficiently integrated into or otherwise used with existing fluid source systems within a hospital or treatment center to avoid the undesired costs and efforts associated with the frequent re-filling or replacing of coolant sources in typical medical cooling systems. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a coolant control and delivery system 14. The medical device 12 may generally include one or more treatment regions for energetic or other therapeutic interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Continuing to refer to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid injection tube 28 traversing at least a portion of the elongate body and towards the distal portion. The injection tube 28 may be coupled to or otherwise extend from the distal portion of the elongate body 16, and may further be coupled to the shaft 22 and/or distal tip of the medical device 12. The fluid injection tube 28 may be flexible, constructed from a shape memory material (such as Nitinol), and/or include other controllably deformable materials that allow the fluid injection tube 28 to be manipulated into a plurality of different geometric configurations, shapes, and/or dimensions.

The fluid injection tube 28 may define a lumen therein for the passage or delivery of a fluid from the proximal portion of the elongate body 16 and/or the coolant control and delivery system 14 to the distal portion and/or treatment region(s) of the medical device 12. The fluid injection tube 28 may further include one or more apertures or openings therein to provide for the dispersion or directed ejection of fluid from the tube to an environment exterior to the fluid injection tube 28.

The medical device may further include a thermal treatment region 30 at or near the distal portion of the device. The thermal treatment region 30 may include a thermally-transmissive section or area allowing thermal exchange with a targeted tissue or region external to the medical device using one or more thermal treatment modalities, such as radiofrequency energy delivery, cryogenic treatment of the tissue for example. As shown in FIG. 1, the thermal treatment region 30 may include an expandable element 32 at the distal portion of the elongate body 16. The expandable element 32 may be coupled to a portion of the elongate body 16 and also coupled to a portion of the shaft 22 and/or distal tip 26 to contain a portion of the fluid injection tube 28 therein. The expandable element 32 defines an interior chamber or region that contains coolant or fluid dispersed from the fluid injection tube 28, and may be in fluid communication with an exhaust lumen 34 defined by or included in the elongate body 16 for the removal of dispersed coolant from the interior of the expandable element 32. The expandable element 32 may further include one or more material layers providing for puncture resistance, radiopacity, or the like. Of note, while the thermal treatment region 30 is described as including an expandable element, other configurations of the thermal treatment region are contemplated, including linear thermal segments, arcuate thermal segments, non-expandable cooling chambers, and the like.

The medical device 12 may include a handle 36 coupled to the proximal portion of the elongate body 16. The handle 36 can include circuitry for identification and/or use in controlling of the medical device 12 or another component of the system. For example, the handle 36 may include one or more pressure sensors 38 to monitor the fluid pressure within the medical device 12. Additionally, the handle 36 may be provided with a fitting 40 for receiving a guide wire that may be passed into the guide wire lumen 24. The handle 36 may also include connectors 42 that are matable to the coolant control and delivery system 14 either directly or indirectly by way of one or more umbilicals. The handle 36 may further include blood detection circuitry in fluid and/or optical communication with the injection, exhaust and/or interstitial lumens. The handle 36 may also include a pressure relief valve in fluid communication with the fluid injection tube 28 and/or exhaust lumen 34 to automatically open under a predetermined threshold value in the event that value is exceeded.

The handle 36 may also include one or more actuation or control features that allow a user to control, deflect, steer, or otherwise manipulate a distal portion of the medical device from the proximal portion of the medical device. For example, the handle 36 may include one or more components such as a lever or knob 44 for manipulating the elongate body 16 and/or additional components of the medical device 12, such as a pull wire 46 with a proximal end and a distal end anchored to the elongate body 16 at or near the distal portion. The medical device 12 may include an actuator element 48 that is movably coupled to the proximal portion of the elongate body 16 and/or the handle 36. The actuator element 48 may further be coupled to a proximal portion of the shaft 22 such that manipulating the actuator element 48 in a longitudinal direction causes the shaft 22 to slide towards either of the proximal or distal portions of the elongate body 16. The actuator element 48 may include a thumb-slide, a push-button, a rotating lever, or other mechanical structure for providing a movable coupling to the elongate body 16, the handle 36, and/or the shaft 22. Moreover, the actuator element 48 may be movably coupled to the handle 36 such that the actuator element is movable into individual, distinct positions, and is able to be releasably secured in any one of the distinct positions.

The system 10 may further include one or more sensors to monitor the operating parameters throughout the system, including for example, pressure, temperature, flow rates, volume, or the like in the coolant control and delivery system 14 and/or the medical device 12, in addition to monitoring, recording or otherwise conveying measurements or conditions within the medical device 12 or the ambient environment at the distal portion of the medical device 12. The sensor(s) may be in communication with one or more components of the coolant control and delivery system 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the coolant control and delivery system 14, as described in more detail below.

Figure 2:
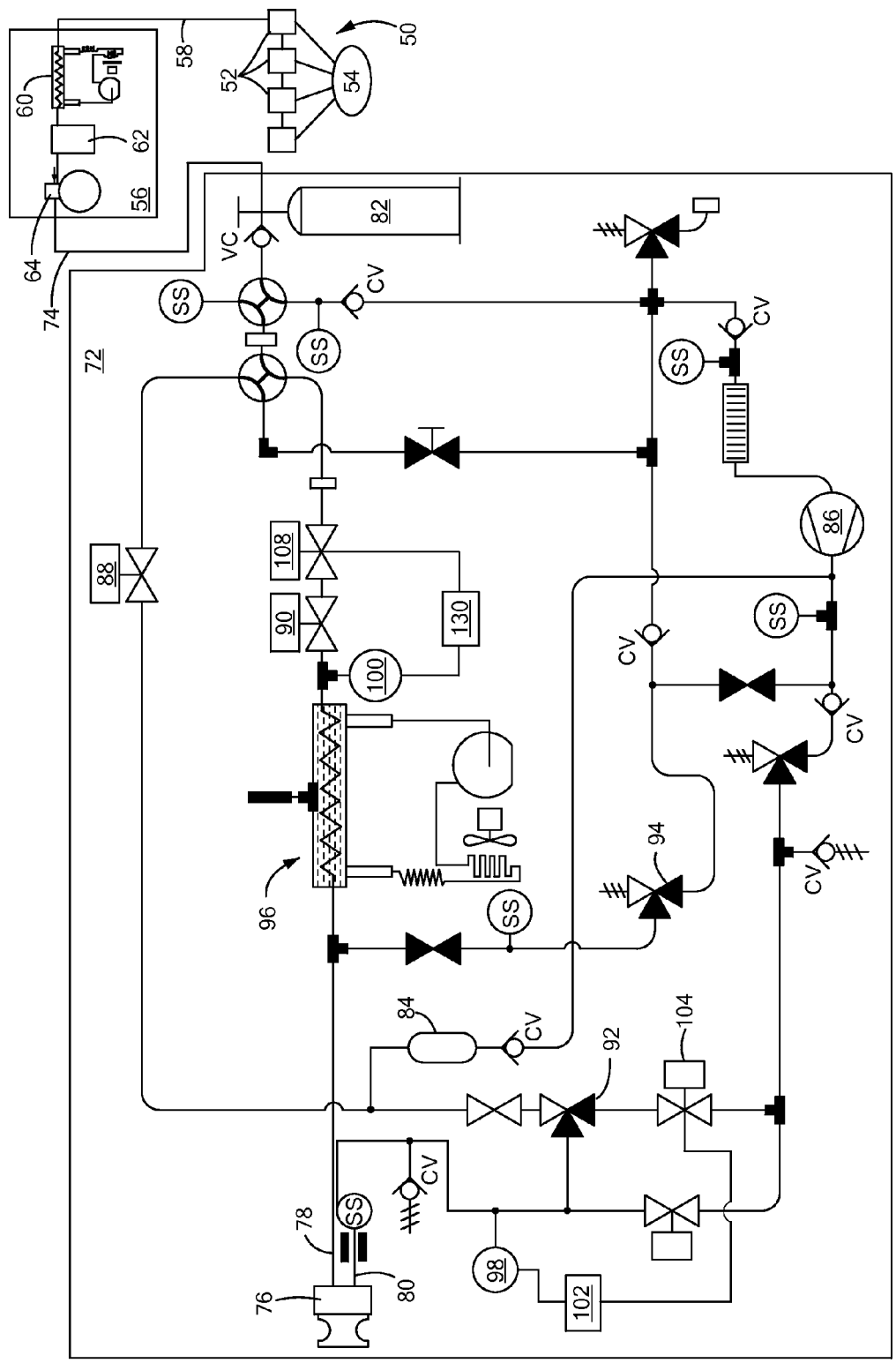
FIG. 2 is a schematic of an embodiment of a medical coolant delivery system for the medical system of FIG. 1.

Turning now to FIG. 2, a schematic of the coolant control and delivery system 14 is shown. In general, the coolant control and delivery system 14 may include pumps, valves, controllers or the like to deliver, recover and/or re-circulate fluid delivered to the handle, the elongate body, and/or the fluid pathways of the medical device 12. The control and delivery system 14 also includes various control mechanisms for the medical system 10, such as one or more controllers, processors, and/or software modules containing instructions or algorithms to provide for the automated operation and performance of the features, sequences, or procedures described herein.

The coolant control and delivery system 14 may obtain a fluid or coolant from a fluid distribution network 50 having a plurality of fluid outlets 52 in fluid communication with a central source 54 to avoid the associated costs and other requirements of maintaining a medical system having a large tank storing fluid or coolant for use with a particular medical device. As used herein, the term "fluid" includes liquids, gases, and mixtures thereof. The fluid distribution network 50 may be integral with a hospital or patient treatment center that routes fluids to a plurality of outlets 52 in individual rooms or locations within the hospital or treatment center. For example, many hospitals include outlets throughout the building providing oxygen, nitrous oxide, or other fluids for on-demand use in the individual rooms or treatment areas, with the central fluid source 54 located in another area of the hospital or treatment center outside of the patient treatment areas.

Although typically used for direct patient inhalation and/or treatment or anesthesia, such available fluids can be conditioned for use as a coolant during a thermal treatment procedure as described herein.

Particularly, the coolant control and delivery system 14 may generally include a fluid conditioning segment or subsystem 56 that manipulates the characteristics of a fluid provided by the fluid distribution network 50 to optimize its use in the medical system 10. The fluid conditioning subsystem 56 may include a fluid inlet line 58 engageable with one of the outlets 52 of the fluid distribution network 50 using one or more connectors. A subcooler 60 may be coupled to the fluid inlet line in thermal communication with a fluid flowing therethrough to lower the temperature of the fluid in the fluid inlet line 58. The subcooler 60 may include a heat exchange assembly or mechanism that transfers heat away from the fluid flowing through the subsystem 56. Examples of such subcooling or heat exchange configurations may include a closed-loop fluid circuit that removes heat from the fluid inlet line using a compressor, condenser, and/or heat exchanger; a Peltier heat transfer device; or other thermal transfer mechanisms and/or temperature reduction components.

One or more adsorbent materials or elements 62 may be disposed within or otherwise coupled to the fluid inlet line to reduce the humidity or moisture content of the fluid flowing therethrough. While moisture or humidity in the fluid provided by the fluid distribution network 50 may be suitable or unproblematic for use as an inhalant for a patient, the moisture in the fluid can cause the creation of ice crystals in a medical system using the fluid as a coolant. The ice crystals can obstruct fluid flow paths within the medical system 10 and can also damage components of the system. Accordingly, the adsorbent element(s) 62 may remove moisture to a designated level to prevent or greatly reduce the formation of ice crystals, such as a moisture level less than 50 ppm for example.

The fluid conditioning subsystem 56 may also include one or more compressors 64 coupled to the fluid inlet line downstream of the subcooler 60 to increase the pressure of fluid received from the fluid distribution network 50 to a level for sufficient use as a coolant in a thermal treatment procedure. For example, the outlet pressure of a fluid, such as nitrous oxide, in a hospital network may be in the range of approximately 20 to 50 psi, while a suitable pressure for use as a cryogenic coolant may be in the range of approximately 500 to 1,000 psig. Accordingly, the compressor(s) 64 may operate to compress a fluid to a pressure level between approximately 500 to 1,000 psig, or otherwise have a compression factor of approximately 15 to 30, or higher.

Figure 3:
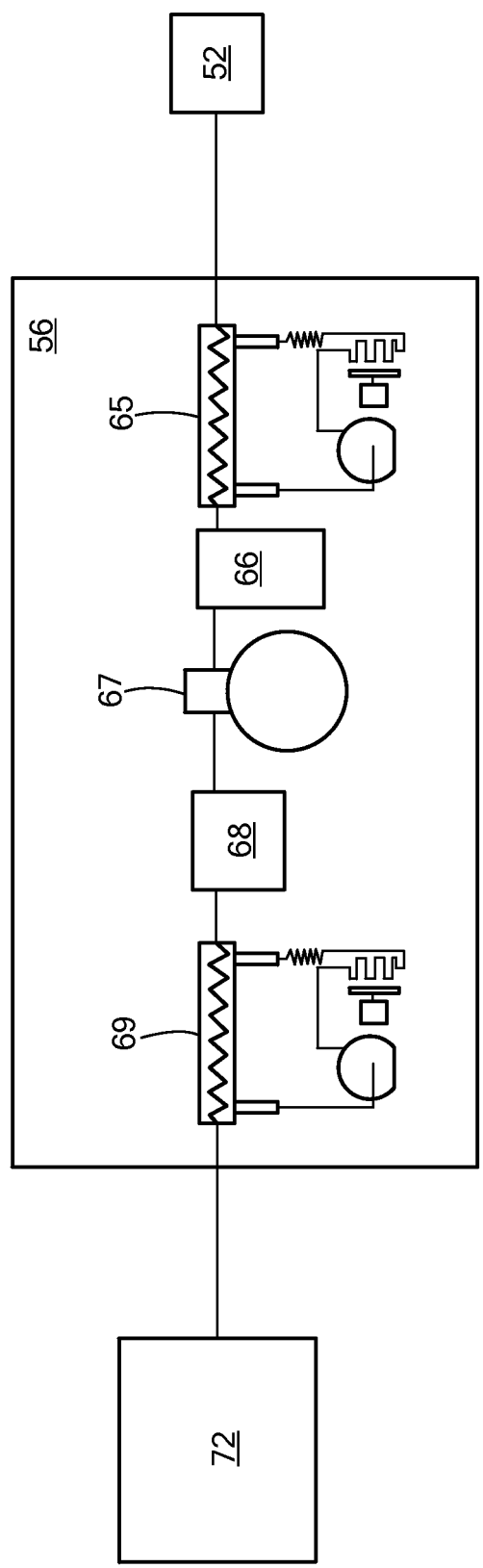
FIG. 3 is an additional schematic of an embodiment of a medical coolant delivery system for the medical system of FIG. 1.

Now turning to FIG. 3, an alternative configuration for the fluid conditioning subsystem 56 is shown. A first subcooler 65 is coupled to a fluid conduit receiving a fluid from the outlet 54. An adsorbent element 66 may also be disposed on or about the fluid conduit to remove moisture as described above, and a compressor 67 is also included to increase the pressure of the fluid in the conduit or inlet line for use by system 10. A radiator or heat exchanger 68 may be located downstream of one or more compressors 68 to allow the compressed fluid to be cooled through thermal exchange with the surrounding air (or another thermal dissipation fluid or material). The fluid conditioning subsystem 56 may also include a second subcooler 69 downstream of the compressor and/or radiator to further cool or otherwise reduce the temperature of the fluid passing through the subsystem 56.

In compressing the fluid received from the outlet 52 by a factor of 15 to 30 (e.g., from approximately 50 psi to 500-1,000 psig), the fluid is heated considerably. For example, if the fluid dispersed by the outlet 52 is at room temperature (or about 20° C., for example), and the fluid is compressed or otherwise has its pressure raised by a factor of 10 to 20, its resulting temperature at the outlet of a compressor will be approximately 280° C. to 300° C. To subsequently use the compressed fluid as a cryogenic coolant to thermally treat tissue with the medical device, the temperature must be lowered, and the fluid may be liquefied. In FIGS. 2-3, the subcooler 60, 65 upstream of the compressor 64, 67 can primarily reduce the temperature of the fluid provided by the outlet from a temperature of approximately 20° C. to a cooled temperature between approximately −80° C. to −20° C. Due to the high compression factor, the compressor 67 may still have an outlet fluid temperature of approximately 200° C. The heated temperature of the fluid exiting the compressor 67 can be passively dissipated by the radiator 68 into the surrounding air or other medium (as shown in FIG. 3). The second subcooler 69 can then reduce the temperature of the fluid even further, which may include inducing a phase change of the fluid from a gaseous or partly-gaseous state to a liquid state, prior to delivering or transferring the coolant to the other segments of the system for later use in the medical device 10. Variations in the placement and quantity of thermal exchange components such as subcoolers or radiators about one or more compressors may be implemented to achieve the increased compression of the fluid while maintaining or achieving a desired operating temperature of the fluid after compression.

Referring again to FIG. 2, the coolant control and delivery system 14 may include a fluid delivery subsystem 72 that selectively controls the circulation and/or delivery of fluid received from the fluid conditioning subsystem 56 to the medical device 12. The fluid delivery subsystem 72 may receive fluid from an outlet line 74 of the conditioning subsystem, and may be coupled to the medical device 12 through a connector 76, which places a supply lumen 78 and an exhaust lumen 80 of the fluid delivery subsystem 72 in fluid communication with the fluid injection tube 28 and exhaust lumen 34 of the medical device 12.

The fluid delivery subsystem 72 may include a first reservoir 82 for the storage of conditioned fluid received from the conditioning subsystem. The first reservoir 82 may have sufficient volume to store enough coolant to complete a designated procedure with the medical device 12, and/or may act as a safeguard or buffer if fluid is drawn continuously from the outlet 52 and conditioning subsystem 56 during a designated procedure. For example, the first reservoir may have a capacity of approximately 1.5 to 2 lbs of fluid or coolant, rather than the large, industrial size reservoirs having a typical capacity of 10 to 20 lbs. The first reservoir 82 can thus allow the conditioning subsystem 56 to operate intermittently or periodically while maintaining or storing enough coolant for a procedure, thereby increasing the efficiency of the medical system 10.

The delivery subsystem 72 may also include a second reservoir 84 having a volumetric capacity smaller than the volumetric capacity of the first reservoir. For example, the second reservoir 84 may have a volumetric capacity of approximately 20 $cm^3$, which has been shown to reduce the likelihood of cardiac abnormalities and/or failure due to coolant egress from a medical device into the vascular system.

A vacuum source 86 in the fluid delivery subsystem 72 may create a low-pressure environment in one or more conduits within the medical system 10 and/or medical device 12 so that fluid is drawn into the conduit(s)/lumen(s) of the elongate body 16, away from the distal portion and towards the proximal portion of the elongate body 16. The vacuum source 86 may include any structure and/or apparatus able to provide a negative pressure gradient for providing fluid flow, including pumps, plunger devices, or the like.

One or more valves may be disposed about the fluid delivery subsystem in fluid communication with the supply lumen 78 and/or the exhaust lumen 80 for manipulating and/or providing fluid flow along a desired path. For example, the fluid delivery subsystem 72 may include a pair of valves, 88 and 90, in fluid communication with the first reservoir 82 such that the first reservoir 82 may be selectively switched from being in fluid communication with the second reservoir 84 to being in fluid communication with the supply lumen 78. Moreover, a valve 92 may be disposed on the exhaust lumen 80 such that the exhaust lumen 80 may be selectively switched from being in fluid communication with the second reservoir 84 to being in fluid communication with the vacuum source 86. In addition, the fluid delivery subsystem may include one or more check valves and/or pressure relief valves CV configured to open to atmosphere or to a recovery tank should a pressure level and/or flow rate within a portion of the medical system 10 exceed a desired or predetermined level.

The fluid delivery subsystem 72 may include a valve 94 in fluid communication with both the supply lumen 78 and the exhaust lumen 80. In particular, the valve 94 may be in fluid communication with the supply lumen at a position upstream of the connector 76, while being in fluid communication with the exhaust lumen downstream from the connector 76. The valve 94 may further be placed in fluid communication with the surrounding atmosphere to equalize pressure in both the exhaust and supply lumens. During operation, the fluid delivery subsystem 72 may detect a failure of the medical device 12, such as an indication of the presence of blood or bodily fluid being entrained into the medical system 10. Upon such detection, coolant flow may be terminated. However, despite the termination of fluid flow, due to the built-up pressure levels in the supply and exhaust lumens, bodily fluid may continue to be siphoned into the medical device and thus into portions of the fluid delivery subsystem. To reduce the likelihood that siphoning occurs, the valve 94 may be actuated to place both the supply lumen 78 and the exhaust lumen 80 into fluid communication with the atmosphere. By doing so, the pressure in either lumen will be substantially equalized and thus will prevent the further ingress of bodily fluids into the medical device and thus the console. Of course, the equalization and/or subjection of both the supply and exhaust lumens may be achieved by using one or more valves in various configuration.

The fluid delivery subsystem 72 may also include a subcooler 96 disposed about a portion of the supply lumen 78 for achieving a desired temperature and/or coolant phase (e.g., liquid) of fluid flowing therethrough. The subcooler 96 may include a compressor, condenser and the like placed in thermal communication with the supply lumen 78.

One or more sensors may be disposed about the supply and exhaust lumens of the fluid delivery subsystem 72 for detecting temperature, pressure, and/or flow rates through a particular portion of the fluid delivery subsystem. For example, a first pressure sensor 98 may be disposed about the exhaust lumen proximate to the connector 76. In addition, a second pressure sensor 100 may be disposed about the supply lumen 78. Of course, additional sensors SS may be included throughout the fluid delivery subsystem 72 for monitoring and/or controlling particular portions of the medical system and operation thereof.

In addition to the one or more sensors, one or more controllers may be coupled to the sensors, and in turn, coupled to one or more of the valves situated throughout the fluid delivery subsystem 72 such that the valves may be controllably manipulated in response to information obtained by the sensors. For example, a first controller 102 may be coupled to the first pressure sensor 98, wherein the first controller 102 is further coupled to a valve 104 disposed on a portion of the exhaust line, and where the valve 104 may also be in fluid communication with the vacuum source 86. In addition, a second controller 130 may be coupled to the second pressure sensor 100, where the second controller 130 is further coupled to a valve 108 disposed about the supply lumen 78. Accordingly, fluid flow through portions of the exhaust and/ or supply lumens may be controllably manipulated in direct response to the information obtained by sensors contained therein. In addition to the one or more sensors, one or more controllers may be coupled to the sensors, and in turn, coupled to one or more of the valves situated throughout the fluid delivery subsystem 72 such that the valves may be controllably manipulated in response to information obtained by the sensors. For example, a first controller 102 may be coupled to the first pressure sensor 98, wherein the first controller 102 is further coupled to a valve 104 disposed on a portion of the exhaust line, and where the valve 104 may also be in fluid communication with the vacuum source 86. In addition, a second controller 130 may be coupled to the second pressure sensor 100, where the second controller 130 is further coupled to a valve 108 disposed about the supply lumen 78. Accordingly, fluid flow through portions of the exhaust and/or supply lumens may be controllably manipulated in direct response to the information obtained by sensors contained therein.

Of note, while the coolant control and delivery system (including its subsystems and components described herein) are illustrated in FIG. 1 as having a single housing, it is contemplated that the components and subsystems described herein may be configured in one or more housings or other enclosures to reduce the amount of space taken up by the system, to reduce operating noise or sound levels produced by the system, to ease installation and/or transport of the system, and/or to selectively couple one or more of the components or subsystems disclosed herein to one or more pre-existing systems or facilities for use (e.g., to retrofit a previously-installed, tank-based fluid delivery system with a fluid conditioning subsystem to allow use of the pre-existing system with an available fluid distribution network).

In an exemplary use, the medical system 10 may be used to thermally treat a targeted tissue region of a patient. In a particular example, the coolant control and delivery system 14 may obtain a fluid flow from the fluid distribution network 50, modify the characteristics of the fluid output of the delivery network 50, deliver the conditioned fluid to the medical device 12, and ablate tissue in proximity to the distal portion 20 of the medical device 12. More particularly, the fluid inlet line 58 of the conditioning subsystem 56 may be connected to an outlet 52 of the fluid distribution network 50 supplying nitrous oxide throughout the network. The conditioning subsystem 56 may cool, compress, de-humidify, or otherwise treat and condition the received fluid (e.g., nitrous oxide) for subsequent use in the thermal procedure by the medical device 12. The conditioning subsystem 56 may be operated continuously during a designated medical procedure or may be run intermittently for a predetermined time period in order to supply sufficient coolant to the first reservoir 82 of the fluid delivery subsystem 72 and/or the medical device 12 for the duration of the selected procedure. The fluid delivery subsystem 72 may then be operated to selectively and controllably deliver the conditioned fluid to the medical device 14. In a particular example, the fluid delivery subsystem 72 may circulate or otherwise deliver the fluid to the medical device through one or more evacuation or flushing phases, inflation phases, transition phases, ablation phases, and/or deflation phases as described in U.S. patent application Ser. No. 12/603,250, filed on Oct. 21, 2009, entitled "DEFLATION MECHANISM FOR A MEDICAL DEVICE," the entirety of which is hereby incorporated by reference.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical fluid conditioning system for use in association with a fluid delivery subsystem and a fluid distribution network, the fluid distribution network having a plurality of fluid outlets in communication with a central fluid supply and the fluid delivery subsystem including a conditioned fluid reservoir and being in communication with a medical device, the medical fluid conditioning system comprising:
 a fluid delivery conduit defining an inlet engageable with one of the fluid outlets of the fluid distribution network and an outlet engageable with the medical device;
 a compressor in fluid communication with the fluid delivery conduit;
 an adsorbent element disposed in the fluid delivery conduit; and
 a subcooler in thermal communication with the fluid delivery conduit,
 the medical fluid conditioning system being upstream of the conditioned fluid reservoir of the fluid delivery subsystem and downstream of the fluid distribution network.

2. The medical fluid conditioning system of claim 1, wherein the fluid delivery subsystem comprises a medical device coupled to the outlet of the fluid delivery conduit.

3. The medical fluid conditioning system of claim 2, wherein the medical device is a cryogenic treatment device.

4. The medical fluid conditioning system of claim 1, wherein the compressor operates to compress a fluid received from the fluid outlet to a pressure between approximately 500 psig to 1,000 psig.

5. The medical fluid conditioning system of claim 1, wherein the adsorbent element reduces a humidity level of a fluid received from the fluid outlet to approximately 60 ppm or less.

6. The medical fluid conditioning system of claim 1, wherein the fluid delivery subsystem further comprises a fluid return conduit engageable with the medical device.

7. The medical fluid conditioning system of claim 6, wherein the fluid delivery subsystem further comprises a vacuum pump coupled to the fluid return conduit.

8. The medical fluid conditioning system of claim 1, wherein the fluid delivery subsystem further comprises a flow meter coupled to the fluid delivery conduit.

9. The medical fluid conditioning system of claim 1, wherein the fluid distribution network is integral within a patient treatment center.

10. The medical fluid conditioning system of claim 1, wherein the fluid distribution network provides nitrous oxide.

11. A method of operating a medical fluid conditioning system, comprising:
 coupling a medical fluid conditioning system to an outlet of a fluid distribution network having a plurality of fluid outlets in a patient treatment center;

coupling the medical fluid conditioning system to a fluid delivery subsystem, the fluid delivery subsystem being in fluid communication with a medical device;

delivering fluid from the outlet of the fluid distribution network to the medical fluid conditioning system;

compressing the delivered fluid with the medical fluid conditioning system;

decreasing the moisture content of the delivered fluid with the medical system to approximately 60 ppm or less with the medical fluid conditioning system;

cooling the fluid with the medical fluid conditioning system;

delivering the fluid from the medical fluid conditioning system to the fluid delivery subsystem;

delivering the fluid from the fluid delivery subsystem to the medical device; and removing the fluid from medical device with the fluid delivery subsystem.

12. The method of claim 11, wherein the fluid is compressed to a pressure between approximately 500 psig to 1,000 psig.

* * * * *